United States Patent [19]

Ueno et al.

[11] Patent Number: 4,973,737
[45] Date of Patent: Nov. 27, 1990

[54] PROCESS FOR PRODUCING BENZYL ESTERS OF AROMATIC HYDROXYCARBOXYLIC ACIDS

[75] Inventors: Ryuzo Ueno, Nishinomiya; Hiroaki Tsuchiya, Kobe; Shigeru Itoh, Nishinomiya; Ichiro Yamamoto, Takarazuka, all of Japan

[73] Assignee: Kabushiki Kaisha Veno Seiyaku Oyo Kenkyuo, Osaka, Japan

[21] Appl. No.: 303,044

[22] Filed: Jan. 30, 1989

Related U.S. Application Data

[63] This application is a continuation of application Ser. No. 06/581,129 filed Feb. 17, 1984.

[30] Foreign Application Priority Data

Feb. 28, 1983 [JP]  Japan .................................. 58-30803

[51] Int. Cl.$^5$ ............................................. C07C 69/88
[52] U.S. Cl. ....................................................... 560/67
[58] Field of Search ........................................ 560/67

[56] References Cited

U.S. PATENT DOCUMENTS 3,332,983  7/1967  Barie, Jr. et al. ...................... 560/67
3,341,570  8/1967  Barie, Jr. et al. ...................... 560/67

*Primary Examiner*—Paul J. Killos

[57] ABSTRACT

Highly pure benzyl esters of aromatic hydroxycarboxylic acids are produced in high yields by reacting an aromatic hydroxycarboxylic acid or its lower alkyl ester with a benzyl alcohol in the presence of an organotin compound of the general formula

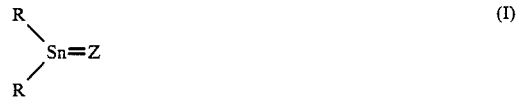

wherein R's are identical or different and each represents an alkyl group having 1 to 8 carbon atoms or an aryl group, and Z represents an oxygen or sulfur atom, an organotin compound of the general formula

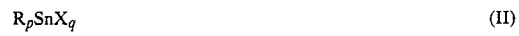

wherein R is as defined, X represents a halogen atom or the group —OCOR$^1$ in which R$^1$ represents a saturated or unsaturated alkyl group having 1 to 18 carbon atoms or an aryl group, p is 2, 3 or 4, q is 0, 1 or 2, the sum of p and q is 4, and when q is 2, the two X's may be linked to each other to form the group —OCO—R$^2$—COO— in which R$^2$ represents a saturated or unsaturated alkylene group having 1 to 10 carbon atoms or an arylene group, or an organotitanium compound of the general formula

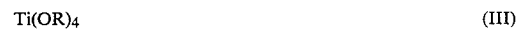

wherein R is as defined.

20 Claims, No Drawings

PROCESS FOR PRODUCING BENZYL ESTERS OF AROMATIC HYDROXYCARBOXYLIC ACIDS

This application is a continuation of application Ser. No. 06/581,129 filed Feb. 17, 1984.

This invention relates to a novel process for producing benzyl esters of aromatic hydroxycarboxylic acids which are useful as color developers for heatsensitive recording materials.

Colorless or light-colored leuco dyes are known to form colors upon reaction with phenols, and this color-forming reaction is utilized in pressure- or heat-sensitive recording sheets. Present-day recorders, printers, facsimiles and the like include heat-sensitive recording systems. The recent advance and sophistication in these devices have led to the need for heat-sensitive recording sheets which form colors at high speeds. Benzyl esters of aromatic hydroxycarboxylic acids, particularly benzyl esters of p-hydroxybenzoic acid, are very important color developers for use in such highspeed heat-sensitive recording sheets because they form colors of high density at high speeds. It is difficult, however, to obtain these compounds in high yields, and industrially, they are now produced only by unsatisfactory methods.

The following methods are known as general esterification reactions for the production of the benzyl esters of aromatic hydroxycarboxylic acids.

(1) Direct esterification of benzyl alcohols and carboxylic acids.
(2) Salt-elimination reaction between benzyl halides and alkali metal salts of carboxylic acids.
(3) Ester-interchange reaction between benzyl alcohols and carboxylic acid esters.

Unlike ordinary esterification reactions, the reaction between benzyl alcohols and aromatic hydroxycarboxylic acids, however, frequently induces undesirable side-reactions.

For example, the method (1) which is most commonly employed and comprises reacting a benzyl alcohol with p-hydroxybenzoio acid in the presence of an acid catalyst has the disadvantage that the yield of the ester is low, and dehydroetherification of the benzyl alcohol occurs to form a large quantity of dibenzyl ether. Moreover, when the reaction temperature is elevated, p-hydroxybenzoic acid is decarboxylated to form phenol. It is extremely difficult in practice, therefore, to synthesize benzyl esters of p-hydroxybenzoic acid by the direct esterification method.

The method (2), for example, comprises reacting benzyl chloride with sodium p-hydroxybenzoate. As an improvement over this reaction, there is known a method in which the reaction is carried out by using dehydrated sodium p-hydroxybenzoate in the presence of a polar non-aqueous solvent such as dimethylformamide or both a non-polar solvent and a phase transfer catalyst Since, however, p-hydroxybenzoic acid is difunctional, the formation of benzyl p-benzyloxybenzoate as a by-product cannot be avoided in this type of reaction, and results in reducing the purity of the final desired compound and complicating the operation of separating and purifying it. Hence, this method is extremely disadvantageous for industrial operation.

The method (3) is a so-called ester-interchange method. Investigations of the present inventors, however, have shown that compounds of zinc, cadmium, calcium, iron, lead, nickel, etc. usually known as effective catalysts for production of polyesters are ineffective for the method (3). Furthermore, since the starting ester is expensive, the method (3) is economically disadvantageous, too.

In short, these known esterification methods for the production of benzyl esters of aromatic hydroxycarboxylic acids are not industrially feasible because of the low yields of the desired compounds and the large amounts of by-products.

The present inventors made extensive investigations on the production of highly pure benzyl esters of aromatic hydroxycarboxylic acids in high yields. These investigations have led to the discovery that certain organotin compounds or organotitanium compounds exhibit outstanding catalytic activity in the production of these benzyl esters.

According to this invention, there is provided a process for producing a benzyl ester of an aromatic hydroxycarboxylic acid, which comprises reacting an aromatic hydroxycarboxylic acid or its lower alkyl ester with a benzyl alcohol in the presence of an organotin compound of the general formula

wherein R's are identical or different and each represents an alkyl group having 1 to 8 carbon atoms or an aryl group, and Z represents an oxygen or sulfur atom, an organotin compound of the general formula

$R_pSnX_q$    (II)

wherein R is as defined, X represents a halogen atom or the group -OCOR$^1$ in which R$^1$ represents a saturated or unsaturated alkyl group having 1 to 18 carbon atoms or an aryl group, p is 2, 3 or 4, q is 0, 1 or 2, the sum of p and q is 4, and when q is 2, the two X's may be linked to each other to form the group -OCO-R2-COO- in which R$^2$ represents a saturated or unsaturated alkylene group having 1 to 10 carbon atoms or an arylene group, or an organotitanium compound of the general formula

Ti(OR)$_4$    (III)

wherein R is as defined.

Examples of suitable aromatic hydroxycarboxylic acids used in the process of this invention include salicyclic acid, m-hydroxybenzoic acid, p-hydroxybenzoic acid, 4-hydroxyisophthalic acid, o-cresotic acid, 1-hydroxy-2-naphthoic acid, 2-hydroxy-3-naphthoic acid, 2-hydroxy-6-naphthoic acid, 2-hydroxy-3-phenylbenzoic acid, 2-hydroxy-5-phenylbenzoic acid, 3-phenyl-4hydroxybenzoic acid, 2-hydroxy-5-isopropylbenzoic acid, 2-hydroxy-5-tert.-butylbenzoic acid and 2-hydroxy-5octylbenzoic acid.

Examples of the lower alkyl esters of aromatic hydroxycarboxylic acids are the methyl, ethyl, propyl and butyl esters of the above-exemplified aromatic hydroxycarboxylic acids.

The benzyl alcohol includes unsubstituted benzyl alcohol and phenethyl alcohol and their derivatives having a substituent such as a halogen atom and an alkyl group on the aromatic ring.

Examples of the organotin compounds represented by general formulae (I) and (II) include dimethyltin oxide, diethyltin oxide, dipropyltin oxide, dibutyltin oxide, diamyltin oxide, dihexyltin oxide, dioctyltin oxide, diphenyltin oxide, dicresyltin oxide, dimethyltin sulfide, dibutyltin sulfide, diphenyltin sulfide, diethyltin diacetate, diethyltin dioctoate, dibutyltin diacetate, dibutyltin dioctoate, dibutyltin dilaurate, dibutyltin dipalmitate, dibutyltin distearate, dibutyltin dioleate, dibutyltin dinaphthenate, dibutyltin dibenzoate, dibutyltin bis(-hydroxybenzoate), dioctyltin diacetate, dioctyltin dioctoate, dioctyltin dilaurate, diethyltin maleate, diethyltin adipate, dibutyltin maleate, dibutyltin fumarate, dibutyltin succinate, dibutyltin adipate, dibutyltin sebacate, diethyltin dichloride, dibutyltin dichloride, diphenyltin dichloride, tributyltin acetate, triphenyltin acetate, triethyltin chloride, tributyltin chloride, triphenyltin chloride, tetraethyl tin and tetrabutyl tin.

Examples of the organotitanium compound of general formula (III) are tetramethyl titanate, tetraethyl titanate, tetrapropyl titanate, tetraisopropyl titanate, tetrabutyl titanate, tetrahexyl titanate and tetraoctyl titanate.

Compounds which catalytically act in the form of the above general formulae during the reaction can likewise be used.

The above catalytic compounds may be used singly or in combination.

The amount of the catalyst used is generally 0.01 to 10% by weight, preferably 0.1 to 4% by weight, based on the weight of the aromatic hydroxycarboxylic acid.

The amount of the benzyl alcohol is preferably 1 to 4 moles per mole of the aromatic hydroxycarboxylic acid. The use of more than 4 moles of the benzyl alcohol does not adversely affect the reaction, but is wasteful because an extra job is required for recovering the benzyl alcohol. If the amount of the benzyl alcohol is less than 1 mole, the yield of the final ester is disadvantageously reduced.

A solvent which forms an azeotrope with water may be used in order to control the reaction temperature or promote dehydration.

In practicing the process of this invention, the aromatic hydroxycarboxylic acid or its lower alkyl ester and the benzyl alcohol are heated in the presence of a catalyst to perform direct esterification. The reaction temperature is 100° to 220° C., preferably 150° to 200° C. The reaction time varies with the amount of the catalyst and the reaction temperature. Usually, it is preferred to set the reaction conditions such that the reaction time becomes 2 to 8 hours. After the reaction, the benzyl alcohol is evaporated under reduced pressure to give a crude benzyl ester. As required, the crude benzyl ester can be easily purified by recrystallization or distillation.

The process of this invention gives the benzyl esters of aromatic hydroxycarboxylic acids having a high purity in high yields. The process is economically advantageous because very simple and inexpensive carboxylic acids are used as starting materials. Furthermore, since the purity of the resulting crude benzyl ester is high, the step of its separation and purification is simple. These advantages make the process of this invention of very great industrial value.

The following non-limitative Examples illustrate the present invention more specifically.

Example 1

69.1 g (0.5 mole) of p-hydroxybenzoic acid, 216.2 g (2 moles) of benzyl alcohol and 1.4 g of dibutyltin oxide were fed into a four-necked glass flask, and reacted at 200° C. for 6 hours with stirring in an atmosphere of nitrogen. Water formed by the reaction and a small amount of phenol resulting from the decomposition of the p-hydroxybenzoic acid were distilled off from the reaction system. After the reaction, the excess of benzyl alcohol was evaporated under reduced pressure to give 111.0 g (yield 94.%) of crude benzyl p-hydroxybenzoate having a purity of 97.4%.

Examples 2 to 11

In each run, a benzyl ester of an aromatic hydroxycarboxylic acid was prepared by repeating the procedure of Example 1 except that the types and amounts of the aromatic hydroxycarboxylic acid, the benzyl alcohol and the catalyst were changed as shown in Table 1, and the reaction conditions shown in Table 1 were used. The yields of the benzyl esters are also shown in Table 1.

TABLE 1

| Example | Aromatic hydroxycarboxylic acid (g) | Benzyl alcohol (g) | Catalyst (g) | Reaction temperature (°C.) | Reaction time (hours) | Yield of the benzyl ester (%) |
|---|---|---|---|---|---|---|
| 2 | p-Hydroxybenzoic acid (69.1) | Benzyl alcohol (216.2) | Dibutyltin oxide (2.8) | 200 | 6 | 95.6 |
| 3 | 2-Hydroxy-6-naphthoic acid (56.4) | Benzyl alcohol (129.6) | Dibutyltin oxide (1.1) | 200 | 4 | 99.4 |
| 4 | p-Hydroxybenzoic acid (69.1) | Phenethyl alcohol (244.2) | Dibutyltin oxide (1.4) | 190 | 6 | 95.0 |
| 5 | p-Hydroxybenzoic acid (69.1) | Benzyl alcohol (216.2) | Dibutyltin diacatate (1.4) | 200 | 6 | 91.6 |
| 6 | p-Hydroxybenzoic acid (69.1) | Benzyl alcohol (216.2) | Dibutyltin dilaurate (1.4) | 200 | 6 | 91.9 |
| 7 | p-Hydroxybenzoic acid (69.1) | Benzyl alcohol (216.2) | Tributyltin chloride (1.4) | 200 | 6 | 90.8 |
| 8 | p-Hydroxybenzoic acid (69.1) | Benzyl alcohol (216.2) | Tetrabutyltin (1.4) | 200 | 6 | 91.4 |
| 9 | p-Hydroxybenzoic acid (69.1) | Benzyl alcohol (216.2) | Tetraisopropyl titanate (0.35) | 195 | 2 | 98.8 |
| 10 | salicyclic acid | Benzyl alcohol | Tetraisoproyl | 190 | 2 | 95.7 |

TABLE 1-continued

| Example | Aromatic hydroxy-carboxylic acid (g) | Benzyl alcohol (g) | Catalyst (g) | Reaction temperature (°C.) | Reaction time (hours) | Yield of the benzyl ester (%) |
| --- | --- | --- | --- | --- | --- | --- |
|  | (69.1) | (216.2) | titanate (2.8) |  |  |  |
| 11 | p-Hydroxybenzoic acid (69.1) | Benzyl alcohol (216.2) | Dibutyltin oxide (0.4) and tetraisopropyl titanate (0.4) | 180 | 6 | 92.5 |

Example 12

69.1 g (0.5 mole) of p-hydroxybenzoic acid, 216.2 g (2 moles) of benzyl alcohol, 0.7 g of tetraisopropyl titanate and 30 g of xylene were fed into a fournecked glass flask, and refluxed for 3 hours with stirring in an atmosphere of nitrogen. During this time, the temperature of the reaction mixture was maintained at 85° C. Water formed by the reaction was removed out of the reaction system by the Dien-Stark's device. The presence of xylene simplified temperature control and promoted removal of water. Benzyl p-hydroxybenzoate was obtained in a yield of 98.7%.

Example 13

152.1 g (1 mole) of methyl p-hydroxybenzoate, 216.2 g (2 moles) of benzyl alcohol and 0.304 g (0.4% based on the weight of methyl p-hydroxybenzoate) of dibutyltin oxide were fed into a four-necked glass flask, and reacted at 200° C. for 6 hours with stirring. Methanol which distilled out during the reaction was recovered for re-use in methyl esterification. After the reaction, the excess of benzyl alcohol was recovered under reduced pressure to give 221.6 g (yield 97.1%) of crude benzyl p-hydroxybenzoate. The ratio of benzyl p-benzyloxybenzoate formed was 1.1%.

Examples 14 to 18

In each run, a benzyl ester was prepared by repeating the procedure of Example 13 using 1 mole of each of the aromatic hydroxycarboxylic acids shown in Table 2, benzyl alcohol in the amount indicated and each of the catalysts shown in Table 2. The results are also shown in Table 2.

TABLE 2

| Example | Aromatic hydroxy-carboxylic acid ester | Amount of benzyl alcohol (moles) | Catalyst | Yield (%) Benzyl ester | Yield (%) Benzyl ester ether |
| --- | --- | --- | --- | --- | --- |
| 14 | Methyl p-hydroxybenzoate | 4 | DBTO (*1) 0.4% (*2) | 98.2 | 0.3 |
| 15 | Methyl p-hydroxybenzoate | 2 | DBTL (*3) 0.4% | 96.4 | 0.2 |
| 16 | Propyl p-hydroxybenzoate | 2 | DBTO 0.4% (*2) | 91.0 | 0.7 |
| 17 | Methyl salicylate | 2 | DBTO 0.4% (*2) | 96.9 | — |
| 18 | Methyl 2-hydroxy-3-naphthoate | 2 | DBTO 0.4% (*2) | 97.3 | — |

(*1):DBTO stands for dibutyltin oxide.
(*2):The percentage based on the aromatic hydroxy carboxylic acid ester.
(*3):DBTL stands for dibutyltin dilaurate.

Comparative Example 1

In the same way as in Example 13, 69.1 g (0.5 mole) of p-hydroxybenzoic acid and 216.2 g (2 moles) of benzyl alcohol were reacted at 120° C. for 4 hours in 138 g of toluene in the presence of 1.44 g of p-toluenesulfonic acid as a catalyst. The yield of benzyl p-hydroxybenzoate was 26%. Dimerization and dehydration of benzyl alcohol occurred simultaneously, and dibenzyl ether was formed in a ratio of as high as 45%.

Comparative Example 2

Example 13 was repeated except that 1.4 g of tin oxide was used as the catalyst. The yield of the benzyl ester was 46.4%.

Comparative Examples 3 to 5

In each run, a benzyl ester was prepared by repeating Example 13 except that zinc acetate or manganese acetate which is an ordinary ester-interchange catalyst was used instead of the alkyltin compound. The results are shown in Table 3.

TABLE 3

| Comparative Example | Aromatic hydroxy-carboxylic acid ester | Amount of benzyl alcohol (moles) | Catalyst | Yield of the benzyl ester (%) |
| --- | --- | --- | --- | --- |
| 3 | Methyl p-hydroxy-benzoate (1 mole) | 2 | Zinc acetate (0.4%) | 44 |
| 4 | Methyl p-hydroxy-benzoate (1 mole) | 2 | Manganese acetate (0.4%) | 48 |
| 5 | Methyl 2-hydroxy-3-naphthoate (1 mole) | 2 | Zinc acetate (0.4%) | 28 |

Referential Example 1

Sodium p-hydroxybenzoate (64 g) and 51 g of benzyl chloride were added to 150 g of dimethylformamide, and reacted at 100° C. for 3 hours. Benzyl p-hydroxybenzoate was obtained in a yield of 74%. The ratio of benzyl p-benzyloxybenzoate, a by-product, formed was 10%.

Referential Example 2

Sodium p-hydroxybenzoate (64 g) and 51 g of benzyl chloride were added to 300 g of xylene, and 1.3 g of tetrabutyl ammonium chloride as a phase transfer catalyst and 2 g of methyl ethyl ketone were added. The mixture was refluxed for 8 hours Benzyl p-hydroxybenzoate was obtained in a yield of 73%, and the ratio of benzyl p-benzyloxybenzoate formed was 13%.

Referential Examples 3 and 4

When direct esterification was carried out using p-toluenesulfonic acid as a catalyst, the yield of the final product was very low. Even when toluene was used as an azeotropic dehydrating solvent, the yield was as low as 26%. In addition, under the reaction conditions employed, a greater portion of the charged benzyl alcohol self-condensed to form dibenzyl ether. The results are summarizd in Table 4.

TABLE 4

| Referential Example | Aromatic hydroxy-carboxylic acid | Amount of benzyl alcohol (moles) | Solvent | Catalyst | Benzyl ester | Benzyl ester ether |
|---|---|---|---|---|---|---|
| 3 | p-Hydroxybenzoic acid (1 mole) | 2 | Toluene | p-Toluenesulfonic acid | 26% | 7%(*) |
| 4 | p-Hydroxybenzoic acid (1 mole) | 2 | None | p-Toluenesulfonic acid | 3% | — |

(*): Dibenzyl ether was simultaneously formed in a yield of 45%.

What we claim is:

1. A process for producing a benzyl ester of p-hydroxybenzoic acid, which consists essentially of the step of reacting p-hydroxybenzoic acid with a benzyl alcohol in the presence of an organotin compound of the general formula

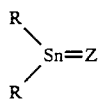 (I)

wherein R's are identical or different and each represents an alkyl group having 1 to 8 carbon atoms or an aryl group, and Z represents an oxygen or sulfur atom,
an organotin compound of the general formula $R_p SnX_q$ (II)

wherein R is as defined, X represents a halogen atom or the group -OCOR$^1$ in which R$^1$ represents a saturated or unsaturated alkyl group having 1 to 18 carbon atoms or an aryl group, p is 2, 3 or 4, q is 0, 1 or 2, the sum of p and q is 4, and when q is 2, the two X's may be linked to each other to form the group -OCO-R$^2$-COO- in which R$^2$ represents a saturated or unsaturated alkylene group having 1 to 10 carbon atoms or an arylene group,
or an organotitanium compound of the general formula Ti(OR)$_4$ (III)

wherein R is as defined.

2. The process of claim 1 wherein the reaction is carried out in the presence of a solvent which forms an azeotrope with water.

3. The process of claim 1 wherein the reaction is carried out in the presence of the organotin compound of formula (I).

4. The process of claim 3 wherein Z represents an oxygen atom.

5. The process of claim 3 wherein Z represents a sulfur atom.

6. The process of claim 4 wherein the organotin compound is selected from the group consisting of dimethyltin oxide, diethyltin oxide, dipropyltin oxide, dibutyltin oxide, diamyltin oxide, dihexyltin oxide, dioctyltin oxide, diphenyltin oxide and dicresyltin oxide.

7. The process of claim 6 wherein the organotin compound is dibutyltin oxide.

8. The process of claim 5 wherein the organotin compound is selected from the group consisting of dimethyltin sulfide, dibutyltin sulfide and diphenyltin sulfide.

9. The process of claim 1 wherein the reaction is carried out in the presence of an organotin compound of the formula (II).

10. The process of claim 9 wherein the organotin compound is selected from the group consisting of diethyltin diacetate, diethyltin dioctoate, dibutyltin diacetate, dibutyltin dioctoate, dibutyltin dilaurate, dibutyltin dipalmitate, dibutyltin distearate, dibutyltin dioleate, dibutyltin dinaphthenate, dibutyltin dibenzoate, dibutyltin bis(hydroxybenzoate), dioctyltin diacetate, dioctyltin dioctoate and dioctyltin dilaurate.

11. The process of claim 9 wherein the organotin compound is selected from the group consisting of diethyltin maleate, diethyltin adipate, dibutyltin maleate, dibutyltin fumarate, dibutyltin succinate, dibutyltin adipate and dibutyltin sebacate.

12. The process of claim 9 wherein the organotin compound is selected from the group consisting of diethyltin dichloride, dibutyltin dichloride and diphenyltin dichloride.

13. The process of claim 9 wherein the organotin compound is selected from the group consisting of tributyltin acetate, triphenyltin acetate, triethyltin chloride, tributyltin chloride and triphenyltin chloride.

14. The process of claim 9 wherein the organotin compound is tetraethyltin or tetrabutyltin.

15. The process of claim 1 wherein the reaction is carried out in the presence of the organotitanium compound of formula (III).

16. The process of claim 15 wherein the organotitanium compound is selected from the group consisting of tetramethyl titanate, tetraethyl titanate, tetrapropyl titanate, tetraisopropyl titanate, tetrabutyl titanate, tetrahexyl titanate and tetraoctyl titanate.

17. The process of claim 1 wherein the reaction is carried out in the presence of from 0.01 to 10% by weight, based on the weight of p-hydroxybenzoic acid, of the organotin compound of formula (I) or formula (II) or the organotitanium compound of formula (III).

18. The process of claim 17 wherein the amount of the organotin compound or organotitanium compound is from 0.1 to 4% by weight based on the weight of p-hydroxybenozic acid.

19. The process of claim 1 wherein the reaction is carried out with from 1 to 4 moles of benzyl alcohol per mole of p-hydroxybenzoic acid.

20. The process of claim 1 wherein the reaction is carried out at a temperature of from 150° to 200° C. for from 2 to 8 hours and wherein the product benzyl ester is obtained in a yield of at least about 90%.

* * * * *